United States Patent [19]

Hubner

[11] Patent Number: 4,885,697

[45] Date of Patent: Dec. 5, 1989

[54] METHOD OF IDENTIFYING SPECTRA

[75] Inventor: Romeo J. Hubner, Wilmington, Del.

[73] Assignee: E. I. Du Pont de Nemours and Company, Wilmington, Del.

[21] Appl. No.: 240,356

[22] Filed: Sep. 1, 1988

[51] Int. Cl.$^4$ .............................................. G06F 15/42
[52] U.S. Cl. .................................... 364/497; 364/498; 324/312; 356/303; 435/34
[58] Field of Search ............... 364/497, 498, 525, 526; 356/300, 302, 303; 324/310, 312; 435/34, 35

[56] References Cited

U.S. PATENT DOCUMENTS

| | | | |
|---|---|---|---|
| 4,365,303 | 12/1982 | Hannah et al. | 364/498 |
| 4,642,778 | 2/1987 | Hieftje et al. | 364/497 |
| 4,651,289 | 3/1987 | Maeda et al. | 364/513.5 |
| 4,717,653 | 1/1988 | Webster, Jr. | 435/5 |
| 4,719,582 | 1/1988 | Ishida et al. | 364/497 |
| 4,753,878 | 6/1988 | Silman | 435/35 |
| 4,766,551 | 8/1988 | Begley | 364/498 |

*Primary Examiner*—Parshotam S. Lall
*Assistant Examiner*—Brian M. Mattson

[57] ABSTRACT

A hierarchial library of spectra representing the point-by-point characteristics of known samples is created. Vectors representing each spectrum are classified according to their similarlity and dissimilarity. Vectors representing unknown samples are compared to known groups of vectors according to similarity until a near match is found.

20 Claims, 11 Drawing Sheets

SPECTRUM OF SAMPLE 1

SPECTRUM OF SAMPLE 2

SPECTRUM OF SAMPLE 3

SPECTRUM OF SAMPLE 4

SPECTRUM OF MARKER FRAGMENT "A"

SPECTRUM OF MARKER FRAGMENT "B"

SPECTRUM OF MARKER FRAGMENT "C"

METHOD OF IDENTIFYING SPECTRA

This invention relates to a method of classifying spectra and using such classification to identify unknowns from their spectra. More particularly, this invention relates to a method of classifying known samples of microorganisms from spectral patterns derived from their DNA and using such classification to identify unknown samples of microorganisms.

BACKGROUND OF THE INVENTION

Microorganisms have traditionally been classified along more or less arbitrary lines based upon selected observable characteristics. While generally satisfactory and historically carried through until today, such classification becomes difficult for unicellular organisms. These and other classification systems have proved crude and ineffectual in view of the present day need for the medical profession to have accurate identification of infectious organisms, viruses and the like.

To overcome some of these problems Webster, Jr. describes in his U.S. Pat. No. 4,717,653 issued Jan. 5, 1988 a method for identifying and characterizing organisms by comparing the chromatographic pattern of restriction endonuclease-digested DNA from the organism, which digested DNA has been hybridized or reassociated with ribosomal RNA information-containing nucleic acid from or derived from a probe organism, with equivalent chromatographic patterns of at least two different known organisms.

The DNA molecule is a polymer shaped like a spiral staircase in which the rails consist of repeating phosphate and sugar groups, and each step is made up of There are only four types of bases: adenine and thymine (A and T), which are always paired with each other; and guanine and cytosine (G and C), which are also paired. A gene, which determines some characteristic of an organism, is simply a stretch of DNA several hundred or thousand bases long.

It is the sequence in which these bases appear that directs a cell's function. Most DNA sequencing procedures attempt to determine the entire sequence of bases in the DNA, while with Webster Jr.'s method the presence of some subsequences with certain conserved characteristics is sought. The first step in the DNA analysis is to segment the DNA molecule. There are several standard methods for doing this, based on restriction enzymes—proteins that "snip" the DNA at specific sites.

The fragments are then sorted by size via gel electrophoresis. In this process, the mixtures containing the fragments are placed in a gel that separates by size, e.g., an agarose gel, and subjected to an electric field that drives the negatively charged DNA fragments towards the positive pole. As the particles move slowly through the gel, the smallest fragments move at a higher speed, and thus arrive first at the opposite end of the gel. After a predetermined time, typically several hours, the electric field is removed.

Webster Jr. discovered that a properly selected labelled probe material may then be hybridized to these DNA fragments after the fragments are made single stranded. The probe material fits onto certain DNA half-fragments much like a piece fits in a jigsaw puzzle. The probe material is labeled with a suitable tag, typically with phosphorous 32. The location of the probe material is then detected through autoradiography, a process in which the radioisotope on the labeled fragments exposes a portion of photographic film.

The end result is an image in which the DNA fragments are arranged in decreasing order of size from one end of the agarose gel to the other. The pattern of radiolabeled fragments, which have been sorted by size, uniquely characterizes the microorganism. This technique has been demonstrated for bacteria and is being extended to other life forms. Thus bacteria, and other higher life forms, may be identified from their DNA rather than from externally observable characteristics.

This photographic image contains a series of bands of varying widths and intensities along parallel linear paths corresponding to the gel electrophoresis lanes. This sheet is scanned with a standard CCD video camera to acquire an electronic image of the radiogram. This image has an appearance very much like a chromatogram containing peaks and valleys varying as a function of distance along the electrophoresis gel. This series of peaks and valleys is unique to the DNA which identifies a particular microorganism. Webster, Jr. suggests in his patent on column 15, line 24 that a user can either compare the obtained band pattern visually or by the aid of a one dimensional computer assisted digital scanner program for recognition of a pattern. The computer memory contains a library or catalog of the different band patterns for a plurality of known organisms. It is now simply a matter of comparing the unknown organism or pattern to the catalog of known patterns to achieve identity of the particular organism.

A related technique, described in U.S. Pat. No. 4,753,878 issued June 28, 1988 to Silman, adds a tag to a microorganism which tag is actively incorporated into the products of metabolism of the microorganism. The the products of metabolism of the microorganism. The products are separated by a gel and the tags detected typically by autoradiography. The emission pattern is detected to provide an electrical signal whose wave pattern or spectra is indicative of the identity of the microorganism. This wave pattern is compared in a computer with patterns stored therein representing a collection of known microorganisms.

In addition to the identification of the characteristic DNA pattern of microorganisms, there are many other instances in which it is desirable or necessary to identify a particular spectra or pattern; for example, U.S. Pat. No. 4,651,289 issued Mar. 17, 1987 to Maeda et al. describes a voice pattern recognition method. The need for pattern recognition extends to many fields including astronomy, mass spectrometry and the like. Maeda et al. describe the similarity method or pattern matching method as being widely used in the field of character recognition. They note that the problem associated with most similarity identification methods is that they require storage for numerous reference patterns and excessive computer time to calculate the numerous matrix calculations needed to analyze and compare the various stored reference patterns and input unknown patterns. Due to the large memory and the large amount of computing time required, a relatively expensive computer typically is required for these operations.

Maeda et al. describe a data base organization and search method using cosines as a similarity metric. The access time using this method is proportional to a fraction of the total number of data base entries and improves somewhat over the existing classical method of comparing the unknown to each element of the entire data base. Unfortunately Maeda et al. still require a relatively high powered computer and a relatively large data base storage capability.

SUMMARY OF THE INVENTION

Many of the deficiencies of these prior art similarity comparison systems for identifying reference patterns or spectra are removed using the method of this invention which affords a reduced identification time proportional to the logarithm of the total number of entries. The invention is a method of establishing a hierarchial library of spectra, each spectrum corresponding to point-by-point representations of the characteristics of a known sample, each spectrum being different from all other spectra, comprising the steps of: (a) converting each spectrum into a vector corresponding to the point-by-point representations of a different known sample; (b) determining the mathematical angles, as determinative of similarity, between all of the vectors, (c) selecting a first vector which is closest to the mean of the vectors and hence represents the center of population of the vectors; (d) selecting a second vector which is most dissimilar to the first vector and represents a local center of population; (e) separating the vectors into first and second groups of vectors that are most similar to the respective selected vectors; (f) for each group of vectors, excluding each previously selected vector representing a center of population and selecting one new vector that represents a local center of population and another vector that is most dissimilar to the one vector and which represents a local center of population of vectors; (g) separating the vectors of each group into pairs of subgroups according to their similarity to the centers of population vectors of step (f); (h) associating the center of population vector for each group of vectors with the center of population vector for each subgroup of vectors; and (i) repeating steps (f), (g), and (h) for each successive subgroup until all vectors have been selected as centers of population.

In a preferred embodiment, the separation of step (g) all vectors within a predetermined mathematical angle of each center of population vector of step (f) are included in each respective subgroup such that some vectors are involved in both subgroups. Preferably, information is stored in the library linking associated vectors; subgroups represented by a selected vector having a link to a common selected vector are merged. Finally the mean of the vectors (C) of step (c) is determined by $C = (c_1, c_2, c_3, \ldots c_N)$ where $c_i = \text{SUM} (p_{ij}/|V_j|)$ where $i = 1, 2, 3, \ldots N$ and $j = 1, 2, 3, \ldots M$, where N is the number of sampling points and p is the value of the sample spectra at each point, M is the number of vectors in the library, and $|V_j|$ is the vector amplitude which is equal to the square root of the sum of the squares of the coordinate values p.

Utilizing this hierarchial library, a spectrum from an unknown sample is identified by the steps of converting the spectrum of the unknown sample into an unknown vector corresponding to a point-by-point representation of the unknown sample; determining the similarity between the unknown vector and the first and second vectors; determining the similarity between the unknown vector and the center of population vectors for the subgroups associated with the more similar one of the first and second vectors; and determining the similarity between the unknown vector and each successive pairs of vectors for the subgroups associated with the more similar higher order subgroup until there are no further associated subgroups, the unknown spectrum being determined by the most similar vector compared.

In conventional spectral data base organizations, the search time requirement is typically proportional to the total number of entries stored in the data base. The organization method of this invention reduces the data base search time to a number proportional to the logarithm of total number of data base entries. This method is aimed at large data bases for rapid access by relatively low performance microcomputers.

The process of organizing the data base is considered to be an offline operation performed periodically, but not by the user, with no concerns with computational overhead. Fast access is of concern to the end user, as is the cost of the computer the data base is accessed from. For the commercial system being visualized the organized data base could be prepared by the system manufacturer and supplied to the customer on computer media such as a disk. As new members of the data base are added this additional data would be distributed to the customer, possibly a subscription basis.

In short, the invention is seen to be a method of identifying an unknown item from its spectrum. The unknown item may be a voice pattern, data from a mass spectrometer, the radiation pattern derived from astronomical objects, and the like, including the spectrum obtained from gel electrophoresis of the distribution of DNA fragments of an unknown bacteria which have been hybridized to a probe material. This DNA fragment spectra data is then compared with the DNA fragment spectra of a library of known bacteria. The library of spectra is organized in a heirarchy that permits identification of the unknown with a minimum number of comparisons. The library organization due to the hierarchial links between library elements facilitates rapid and accurate identification of an unknown with a minimum of computer resources. The method makes fewer comparisons, and uses less computer resources than prior art methods thus facilitating the use of low cost microcomputers. This is a particular advantage since libraries of spectral data of this type are necessarily quite large to be commercially useful.

BRIEF DESCRIPTION OF THE DRAWINGS

The invention may be more fully understood from the following detailed description thereof taken in connection with the accompanying drawings which form a part of this invention description and in which similar reference numbers refer to similar elements in all figures of the drawings in which.

DETAILED DESCRIPTION OF THE PREFERRED EMBODIMENT

The method of this invention involves essentially two major steps. The first of these steps is the organization of the spectra library and the second is the identification of the spectrum of an unknown item using the library. As noted above, the spectra may be identified as any pattern such as a voice pattern, bar code pattern, spectra data emitted by an astronomical body and the like. Since this invention is particularly directed to the solution of the spectral identification method described in or useful with the Webster, Jr. patent, it will be described in this context. It shall be understood however that the invention is not so limited and any spectra may be so identified.

Figure 1A:
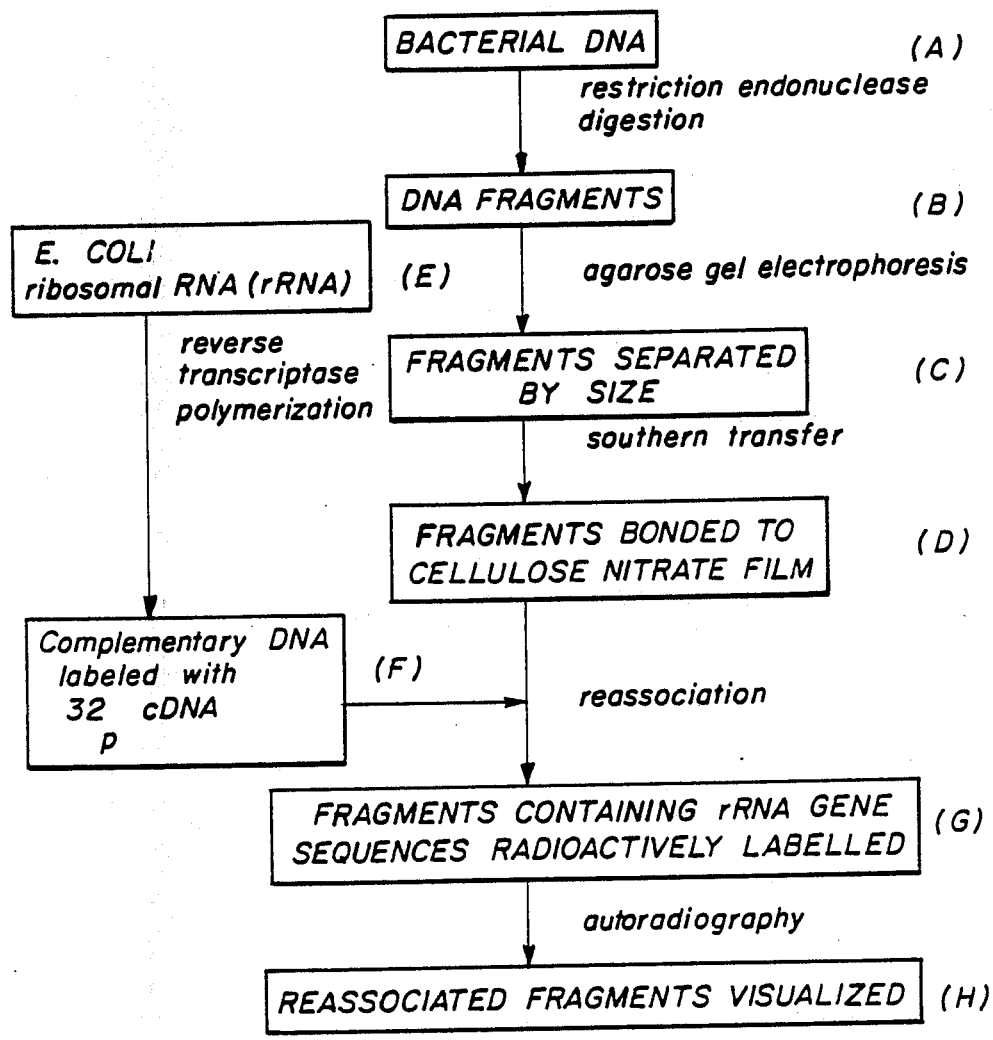
FIGS. 1A and 1B is a block diagram depicting the various steps in processing bacterial DNA to obtain a spectrum of its DNA needed to establish a hierarchial library of spectral data and identify unknown spectra.
Figure 1B:
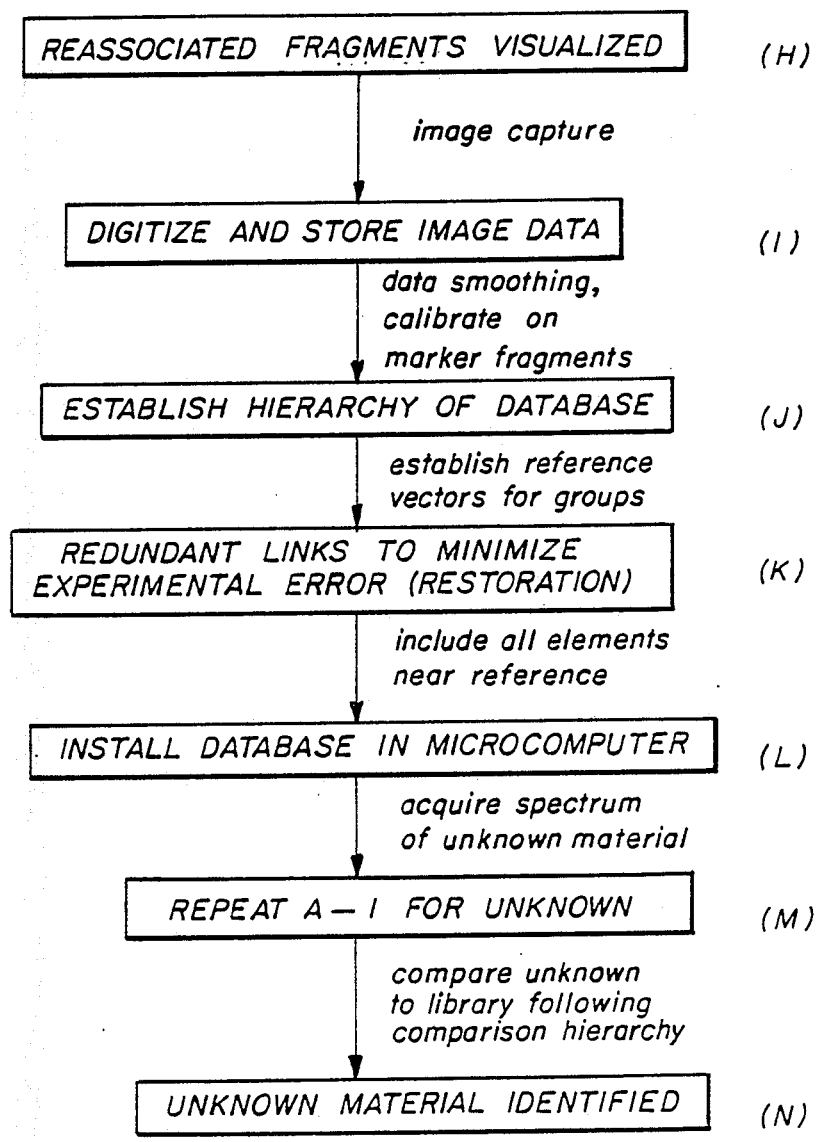

The method will be described particularly with respect to FIGS. 1A and 1B. Thus the bacterial DNA to be identified or processed for use in the hierarchial library, as described by Webster, Jr. is segmented using restriction enzymes which "cut" the DNA at specific sites to produce DNA fragments. These fragments are then sorted by size using conventional gel electrophoresis. In this case an agarose gel may be used and the fragments subjected to an electric field that drives the negatively charged fragments to its oppositive pole. As the fragments move slowly through the agarose gel, the smallest fragment moves at the higher speed, and thus arrives at the opposite end of the agarose gel first.

The gels are then stained as is otherwise well known in the art and standardized as to the fragment sizes using standard curves constructed with fragments of known size. Separated fragments are then transferred to cellulose nitrate paper by the Southern Blot Technique and covalently bound thereto by heating. The fragments containing the rRNA gene sequences are then located, by the capacity to hybridize with a nucleic acid probe containing rRNA information. The nucleic acid probe can be either nonradioactively labelled or preferably radioactively labelled. When radioactively labelled, the probe can be ribosomal RNA (rRNA), or radioactively labelled DNA which is complementary to the ribosomal RNA (rRNAcDNA), either synthesized by reverse transcription or contained on a clone fragment, which can be labelled, for example, by nick translation.

Next the cellulose nitrate film containing the fragments with rRNA gene sequences radioactively labelled are visualized by placing the cellulose nitrate film against an X-ray film such that the pattern of the radioactive labels is developed on the X-ray film by autoradiography, a well known technique.

The end product of this technique is a chromatographic band pattern or spectra having light and dark regions of various intensities at specific locations. These locations can be readily matched to specific fragment sizes (in kilobase pairs) by introduction into the separation technique of a marker such as EcoR I digested λ bacterio-phage DNA. In this manner both the relative positions of the bands to each other as well as the absolute size of each band can be readily ascertained. The band pattern of the unknown is then compared with the band patterns present in the computer library as will be described. This band pattern is depicted most clearly in FIG. 2 in which four different samples with different markers are illustrated and represented by their respective electrophoretograms.

The resulting radiogram, which may have images from one or more samples of bacterial DNA fragments, is placed in the field of view of a CCD line scan camera for digitization of the image. The operator positions the radiogram such that the line to be scanned by the camera is centered along the axis of the first electrophoresis lane of a sample.

The line is scanned and the intensity level of each point or picture element (pixel) of the camera is converted to a digital value. The image intensity or radiogram density is typically measured with a resolution of 4096 levels (12 bits). There are typically 1024 pixels measured along each lane.

The digitized data is stored in a suitable memory and then processed, using known image processing techniques, such as background removal and amplitude scaling.

Pairs of adjacent pixels are averaged together and these average values represent the density of the radiogram as a function of position along each lane. Since image density is a function of the fragment population, this set of numbers is an uncalibrated spectrum of DNA fragment length. This set of numbers is typically comprised of 512 values. These steps are repeated for the second and subsequent electrophoresis lanes of a sample on the radiogram.

The location of the origin and the fragment length dimensional scale is determined for each lane by measuring the locations of the marker fragments in the adjacent lanes. These subsequent lanes, which contain several marker DNA fragments of known length, are used as rulers to measure the first lane. By measuring the distances between several known markers, both the scale factor for fragment length and the location of the origin of the first lane are calculated.

The numeric values of the first lane are then scaled to calibrate them to fragment length. This calibrated set of numbers representing image density versus fragment length is the calibrated spectrum, but is simply referred to as "the spectrum" of that sample.

A library of spectra is created by processing a number of types of known bacteria samples using steps A–I. This library of spectra is stored in a suitable memory. The set of numbers representing each known spectrum is called an element of the library. To efficiently identify an unknown by comparing it to elements of the library, the library must be organized so that a minimum number of comparisons will result in the correct identification. This organization process is described in steps J–N.

Each spectrum of the known samples is treated mathematically as a vector. The numeric value for each fragment length of a spectrum is considered to be one coordinate value in a multidimensional vector space. Each vector is then compared to all the others and the mathematical angles between pairs of vectors are calculated. Two vectors are said to be similar if this angle is small and dissimilar if the angle is large. Because of mathematical constraints the angle cannot exceed 90 degrees.

A mean vector, which represents the "center" of the population of known samples is calculated. The vector within the population that is nearest to this mean vector is considered to be the center vector and is used as the starting point for comparison purposes. In later steps, when comparisons are being made, a "local" center of population is determined. The local center of population is the one vector in a group (or subgroup) of vectors that is nearest to the mean vector of that group. The vectors of known samples also are ranked according to dissimilarity with the others.

In each step of the analysis, two "reference" vectors are selected: one vector which is most similar to the local center of population and another vector which is least similar to that center. Each of these references will have a subgroup of similar vectors associated with it. Some elements, which are not clearly more similar to one of the references, will be associated with both references. After a vector is selected as a reference, it is set aside and eliminated from further comparisons. The reference vector of one step becomes the local center of population for comparisons of the next step.

The subgroups are then again processed. Each time two new references will be selected. "Links" are established between each of the two new references and the reference of the previous step. This process is repeated until all the elements of the library have been selected as references and linked. The links establish the order in which comparisons will be made when unknowns are later identified.

As used herein the term "associated" means that a hierarchical relationship is established between vectors. These "associated" vectors are linked; their relationship to each other in the hierarchy may be stored in a table.

All laboratory methods are known to introduce some experimental error. The experimental error arising from the gel electrophoresis and from the image digitization introduces a small uncertainty of the true vector position of each element in the library. These errors, if not accounted for, might lead to some erroneous reference links being established. This, in turn, might lead to erroneous identification of an unknown. To overcome the adverse effects of these experimental errors, all elements within a predetermined angular distance of a reference are included in the subgroup associated with that reference. Including these 'nearby' elements in these subgroups provides a redundancy that tends to eliminate the adverse effects of experimental error. This process is called "restoration".

Eventually some elements having multiple associations will be selected as references for two or more subgroups of elements. Under these circumstances, these subgroups are merged and further processed as a single subgroup.

When all elements have been selected as references and linked to other references, this library organization procedure is concluded.

An unknown to be identified is processed using the steps set forth above. The spectrum that is obtained is compared to the vector which is the local center of population of all vectors. The unknown will be found to be more similar to one of the first two reference vectors. The links of this reference vector will determine which references are next to be used for comparison. This process will continue until there are no more reference links remaining for further comparison. The unknown is determined by using a least square fit procedure on the most similar spectra.

Figure 2:
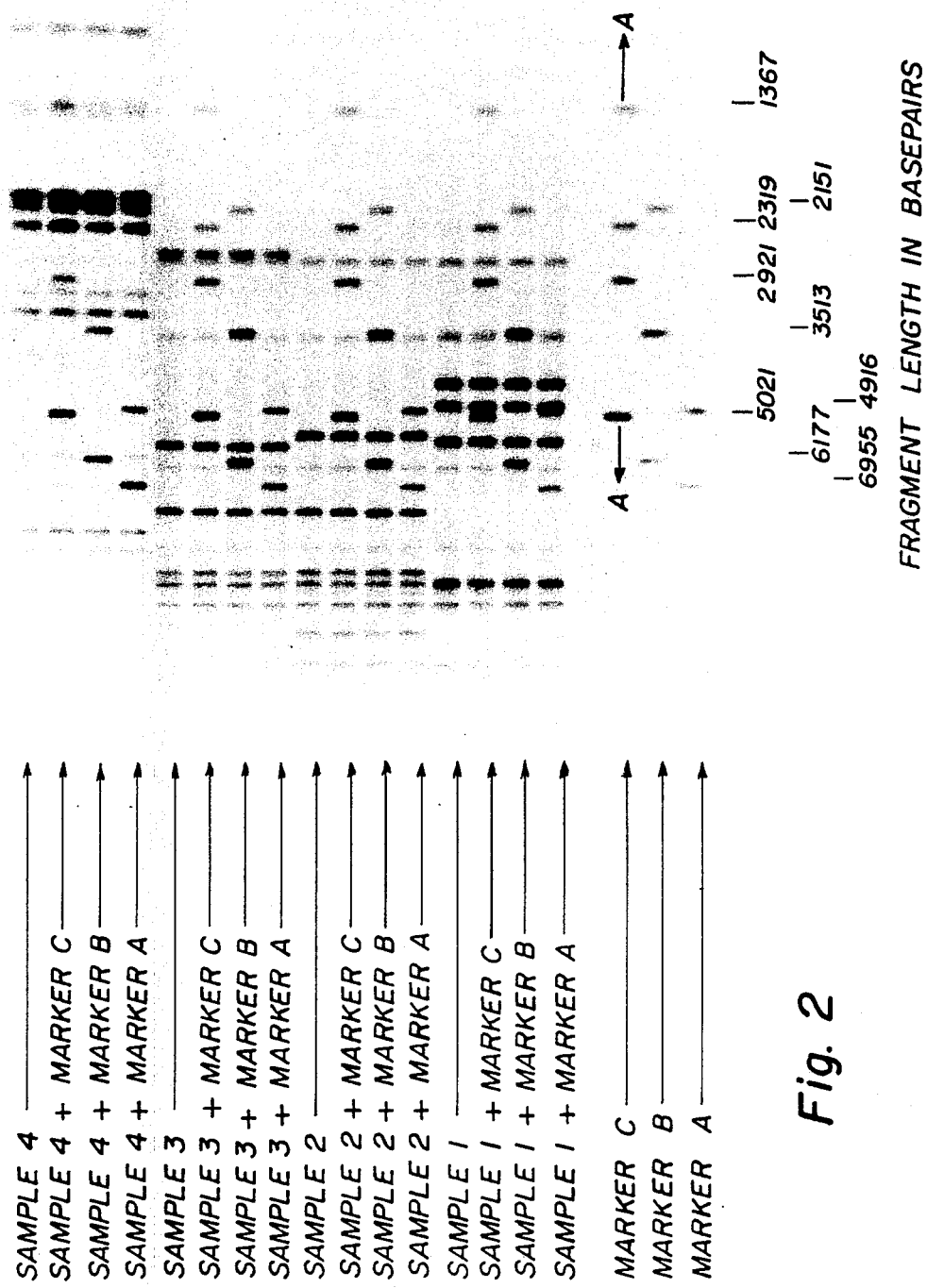
FIG. 2 is a typical gel electrophoresis image obtained using the Webster process in the method of this invention.

The spectrums of the several samples illustrated in FIG. 2, together with their marker fragments are depicted respectively in FIGS. 4 through 10 in which the size of the fragments in base pairs is plotted according to the distance along the electrophoresis gel in kilobase pairs and the amplitude represents the quantity or intensity of each fragment corresponding to the various base pair locations.

Figure 3:
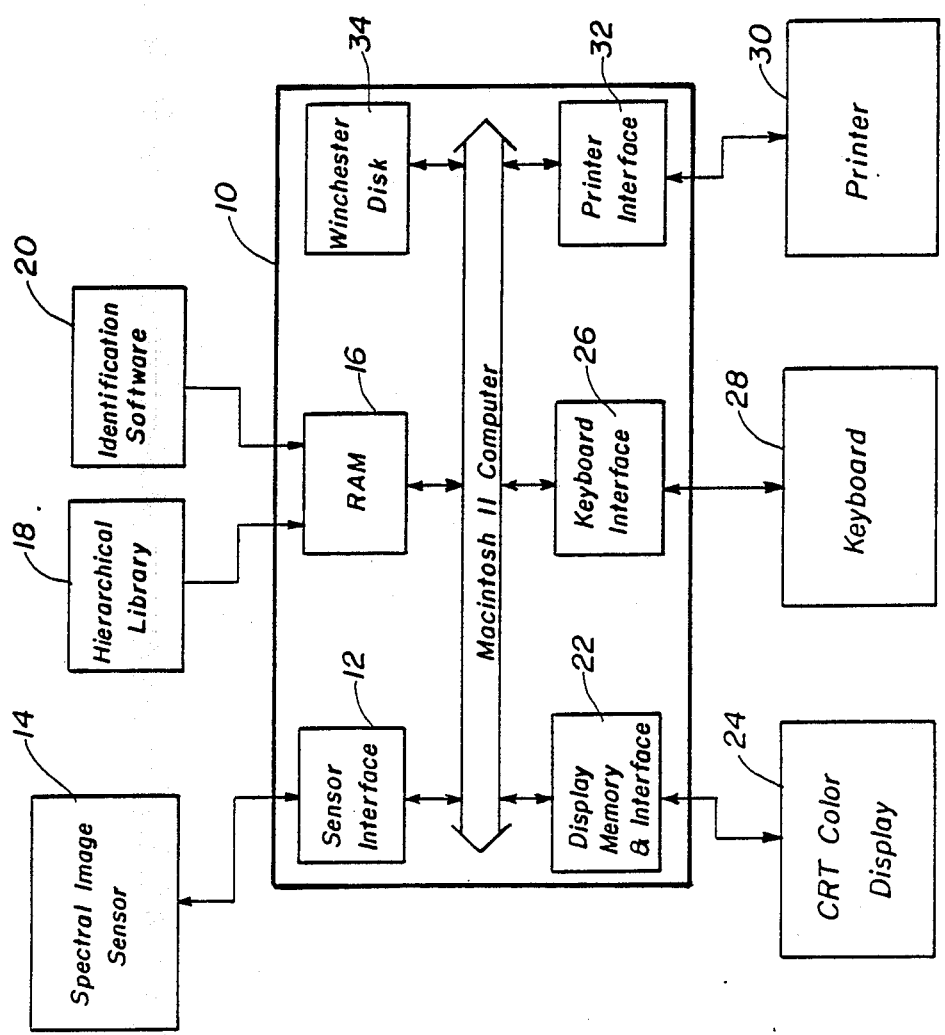
FIG. 3 is a block diagram of a microcomputer that may be used to implement the method of this invention.
Figure 4:
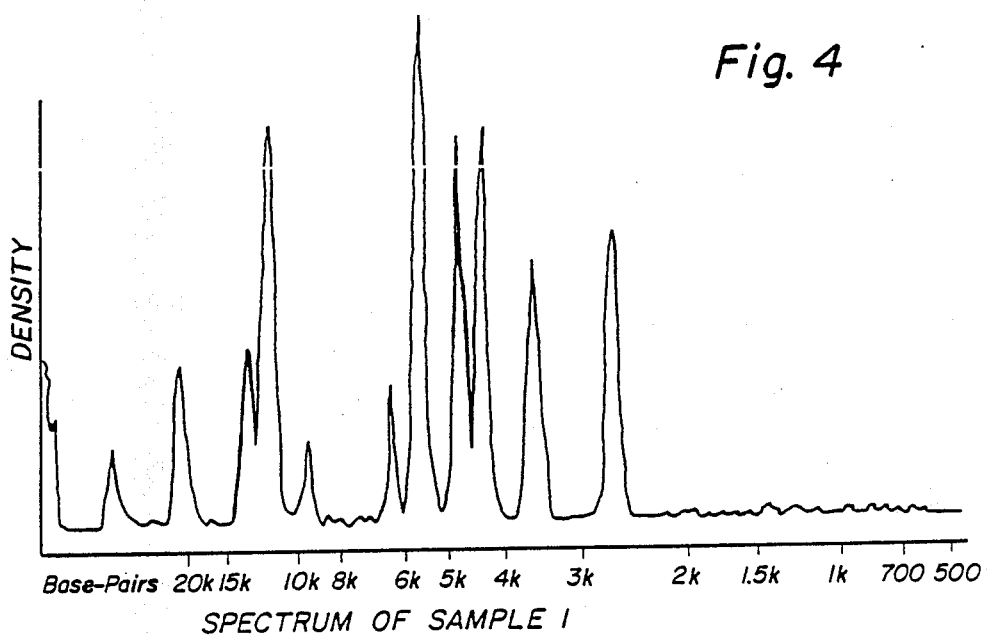
FIGS. 4 through 10 are spectrograms of the various elements of the samples shown in FIG. 2 in which amplitude or density of the electrophoretogram is plotted as the ordinant and the number of base pairs is plotted as the abscissa.
Figure 5:
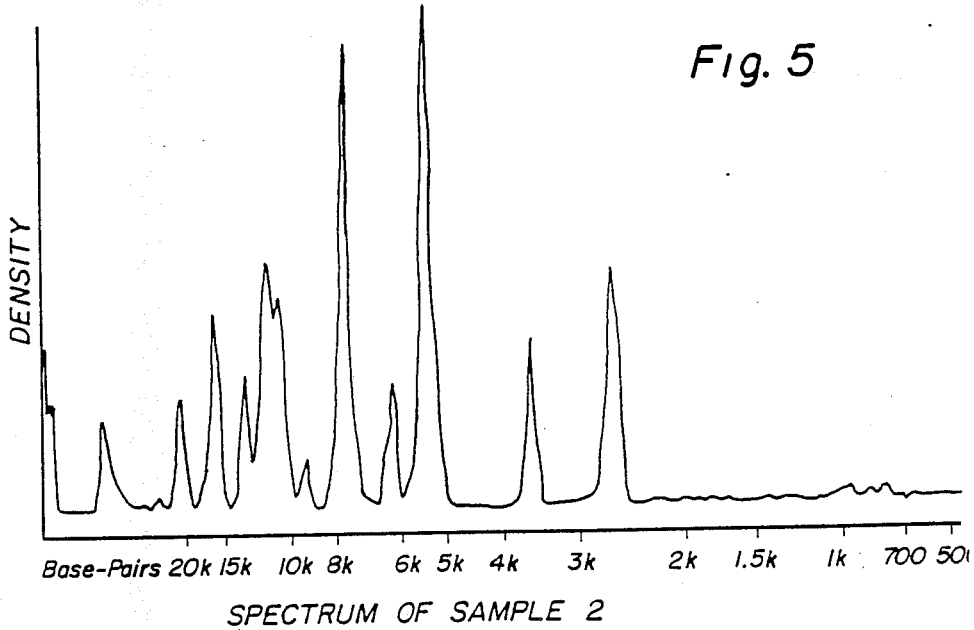
Figure 6:
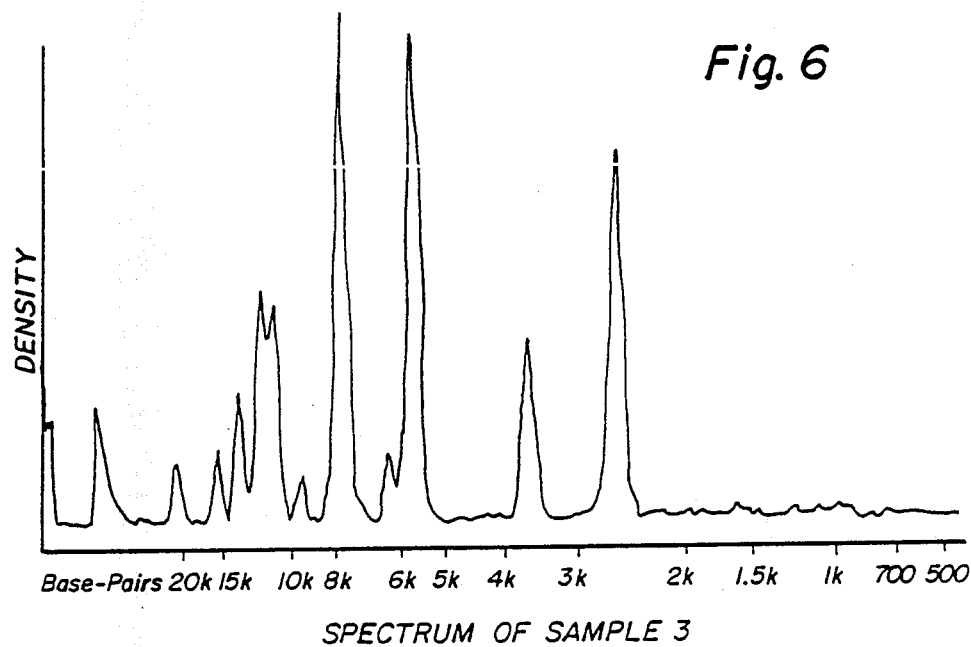
Figure 7:
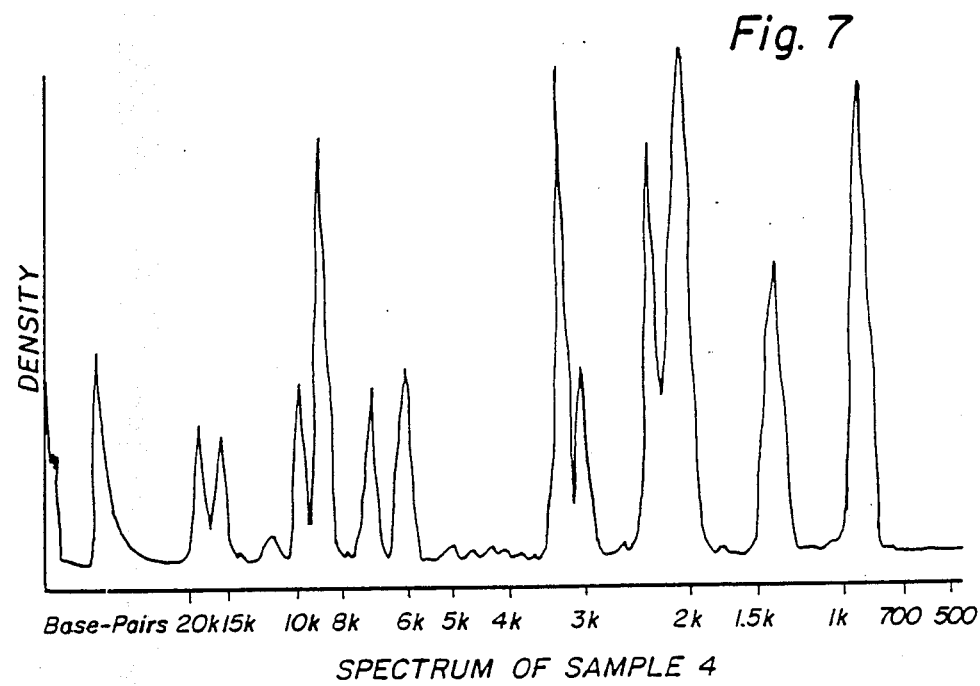
Figure 8:
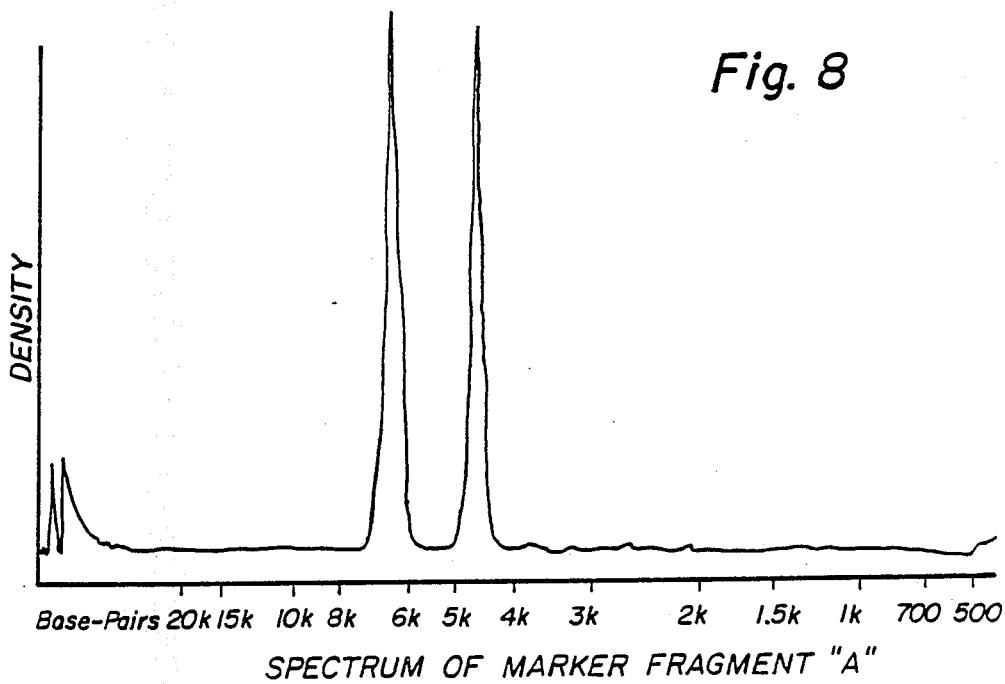
Figure 9:
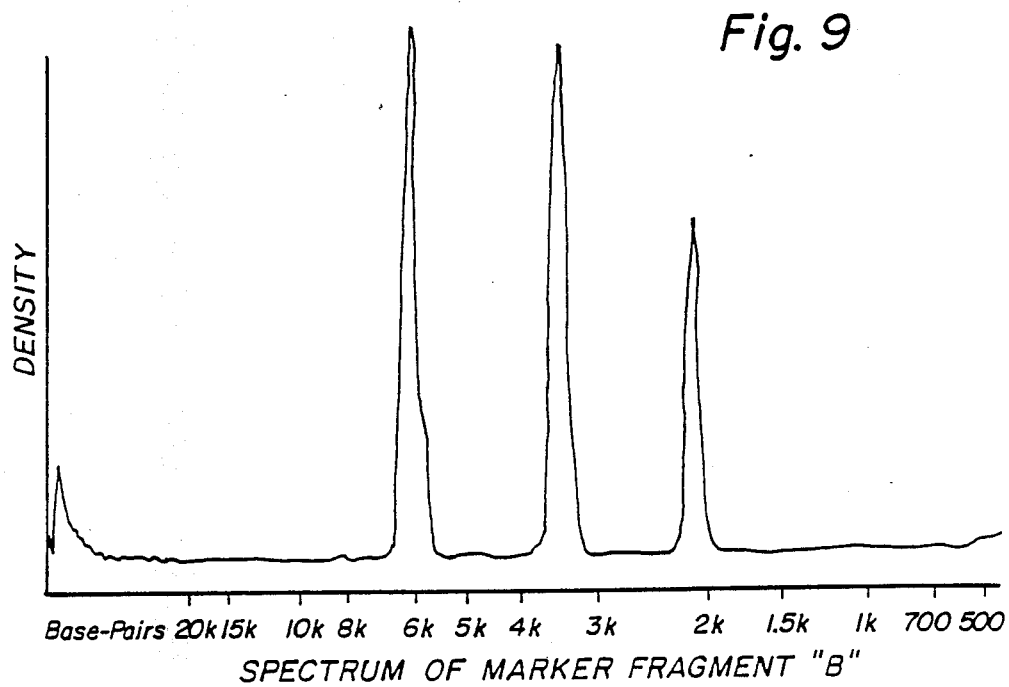
Figure 10:
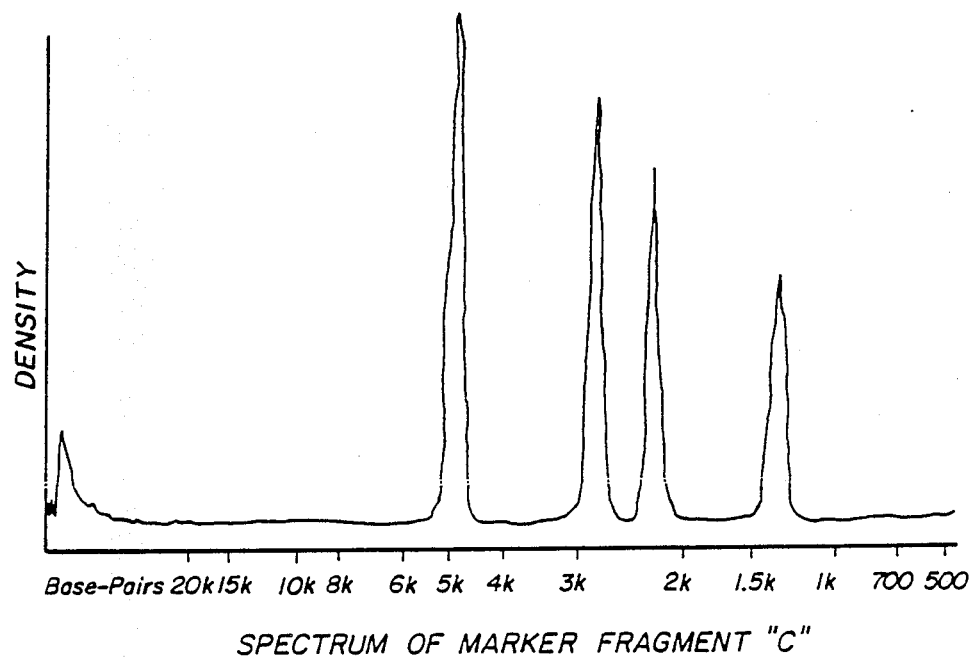

The hardware that may be used to implement the method of this invention is shown in FIG. 3 in block diagrammatic form. This hardware will typically include a microcomputer such as a Macintosh II computer 10 which includes a sensor interface 12 which interfaces with a standard CCD line scan camera or a spectral image sensor 14. The microcomputer also includes a random access memory 16 for interacting with a hierarchial library 18 which will be provided in accordance with this invention and identification software 20. The computer 10 also includes a display memory and interface 22 which interacts with the CRT color display 24, a keyboard interface element 26 which interacts with the keyboard 28 and a printer 30 which interacts through a printer interface module 32. The computer finally will include a hard drive 34 such as a standard Winchester disk.

The sheet of processed film or radiogram is typically illuminated in a transmission mode arrangement and placed in the field of view of the spectrum image sensor 14. The operator enters the identification number of the sample and commands and instructs the computer to acquire the image which is digitized and transferred to the RAM memory 16 of the computer for processing. A digitized image is simultaneously displayed to the operator on the CRT. The operator selects a particular name of the image to be processed by positioning an electronically cursor at appropriate points on the display and commanding the computer to process that portion of the image. Before processing a particular spectrum corresponding to a particular sample, several known image processing operations are performed. Thus, a data smoothing procedure is used to remove random noise from the image data. Sequential pairs of the resulting picture elements are then averaged together to reduce the number of data elements.

A background removal procedure is used to remove intensity variations resulting from differences in overall film density and camera illumination level. Spectrum alignment per molecular weight is obtained by identifying the intensity peaks of the marker fragments and then extrapolating the molecular weight scale from these known points. After scaling, these marker fragments may be subtracted from the image data.

Alternatively, the digital image data for a particular spectra may be obtained through an area camera instead of a CCD camera as just described. With an area camera, the image data is processed to identify the electrophoresis lanes to locate the center line or axis of each line and to measure the width of each lane corresponding each sample.

The central region of each lane, along the lane axis and comprising one third the total lane width is identified. Pixels within this central region are averaged to obtain a single density value for each position along the lane axis. This is done by calculating the mean value for pixels within the central region lying along a line orthogonal to the lane axis. These average values are stored to represent the density values of the image for each position along the lane axis.

The mathematical concepts underlying the method of this invention are based upon the fact that each spectrum is a set of numbers, each of which represents the optical density of a picture element (pixel or point) on an autoradiogram. The points of interest are long the line A—A (FIG. 2) in the direction of migration of the fragments. The autoradiogram, in turn, is a contact X-ray image of a membrane to which the size separated DNA fragments were attached. The sensitized areas of the X-ray image denote the presence of the radioactive label attached to the probe which selectively hybridizes to some of the DNA fragments. The digitized optical density, therefore, represents a measure of the population density of the size separated hybridized DNA fragments.

The spectrum may be mathematically thought of as a vector, where the density values of each point represent the coordinate values of the vector along each axis in a multidimensional space, called a hyperspace because it cannot be represented physically. The number of points determines the number of dimensions in the hyperspace. The density values are stored in the computer as a set of numbers.

The vector is represented by the letter "V" and the points by the small letter "p" followed by a numbered subscript.

$$V = (p_1, p_2, p_3, \ldots, p_N)$$

where N is the number of sampling points and p is the optical density value.

For computation purposes, each vector "V" is normalized to the unit vector "v", as follows:

$$v = (p_1/|V|, p_2/|V|, p_3/|V|, \ldots, p_N/|V|)$$

where "$|V|$" is the vector amplitude or length and is equal to the square root of the sum of the squares of all the coordinate values "p".

$$|V| = \mathrm{SQRT}(\mathrm{sum}(\mathrm{square}(p_i)))$$

where $i = 1, 2, 3, \ldots, N$

The vector sum "C" of all the members of the data base, which represents the population center of gravity of the sample hyperspace, is calculated by using $$C = (c_1, c_2, c_3, \ldots, c_N)$$

where $c_i = \mathrm{SUM}(p_{ij}/|V_j|)$
where $i = 1, 2, 3, \ldots, N$ and $j = 1, 2, 3, \ldots, M$, M being the number of vectors (or spectra) in the data base.

Similarity of two vectors, or proximity in vector space, is defined as the inner product of the vectors and calculated using $$(C, V) = \mathrm{SUM}((p_i/|V|) \ast (c_i/|C|))$$

where $i = 1, 2, 3, \ldots, N$.

The similarity value is never negative due to the constraint of positive optical densities and has an upper bound of 1.0 since, by definition, only unit vectors are compared.

The inner product (C, V), in a more familiar concept, is the cosine of the angle between the two vectors and is also called the direction cosine. An angle of 90 degrees between two vectors produces a similarity value of $\cos(90) = 0.0$ and these vectors are said to be orthogonal or maximally dissimilar. Conversely, an angle of 0 degrees produces a value $\cos(0) = 1.0$ and the vectors are said to be identical or maximally similar.

The inner product is the only similarity metric concept used in the development of the present method and is the value upon which each algorithm decision is based.

In multi-component unknown spectra, the unknown U is considered to be a linear combination of its components V. The unit vectors are related by the formula:

$$u = \mathrm{SUM}(a_k \ast v_k)$$

where $k = 1, 2, \ldots K$ (the number of components).

The coefficients "a" are calculated and represent the relative contribution of a normalized spectrum "v" to the normalized unknown "u". The computational procedure is reduced to the inversion of a matrix where the elements are similarity metric values $$M_{ij} = (V_i, V_j) \text{ and } M_i = (v_i, U)$$

where $i, j = 1, 2, \ldots, K$ (the number of components).

Figure 11:
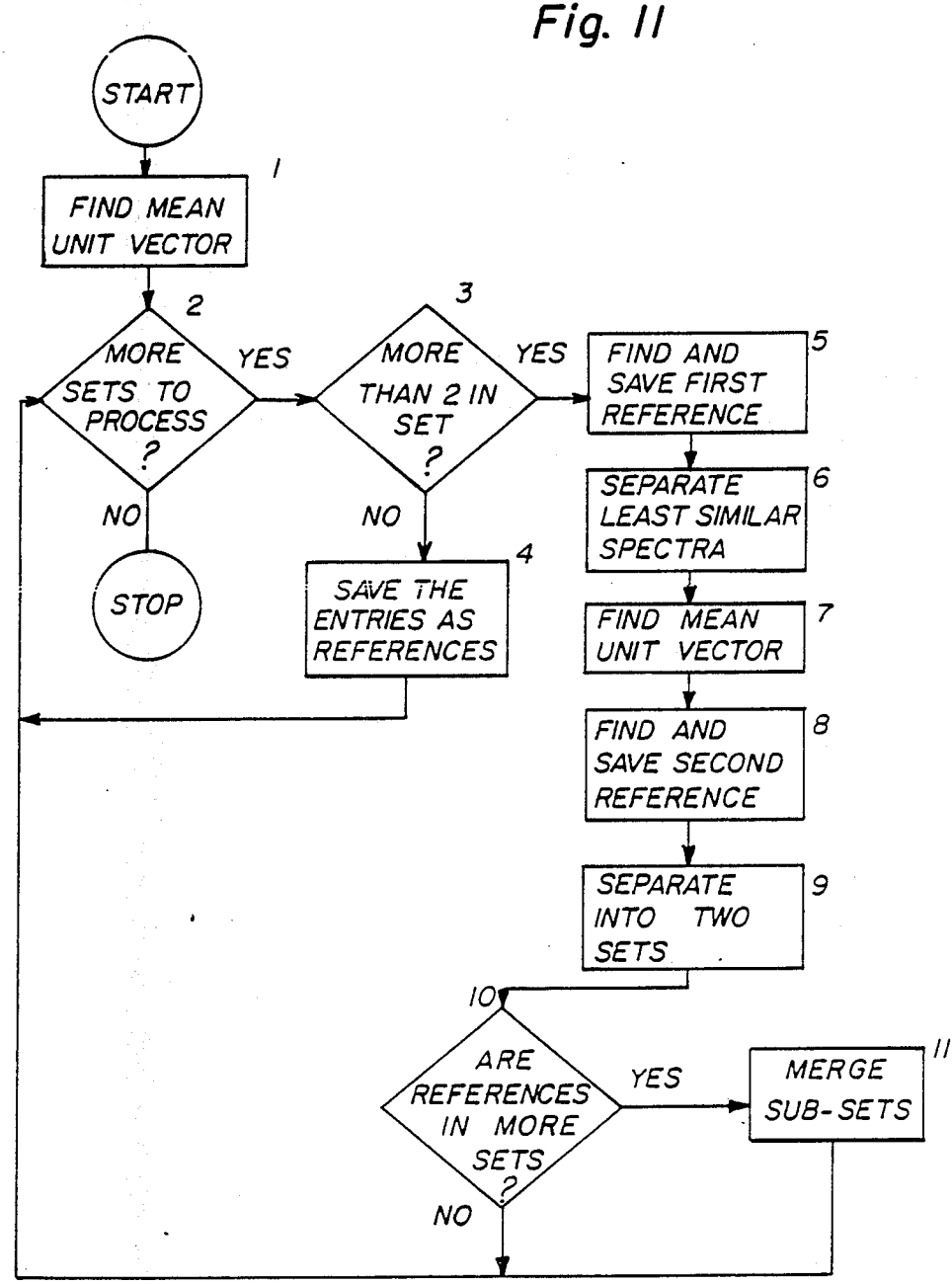
FIG. 11 is a flow chart of the data base organization method of this invention.
Figure 12:
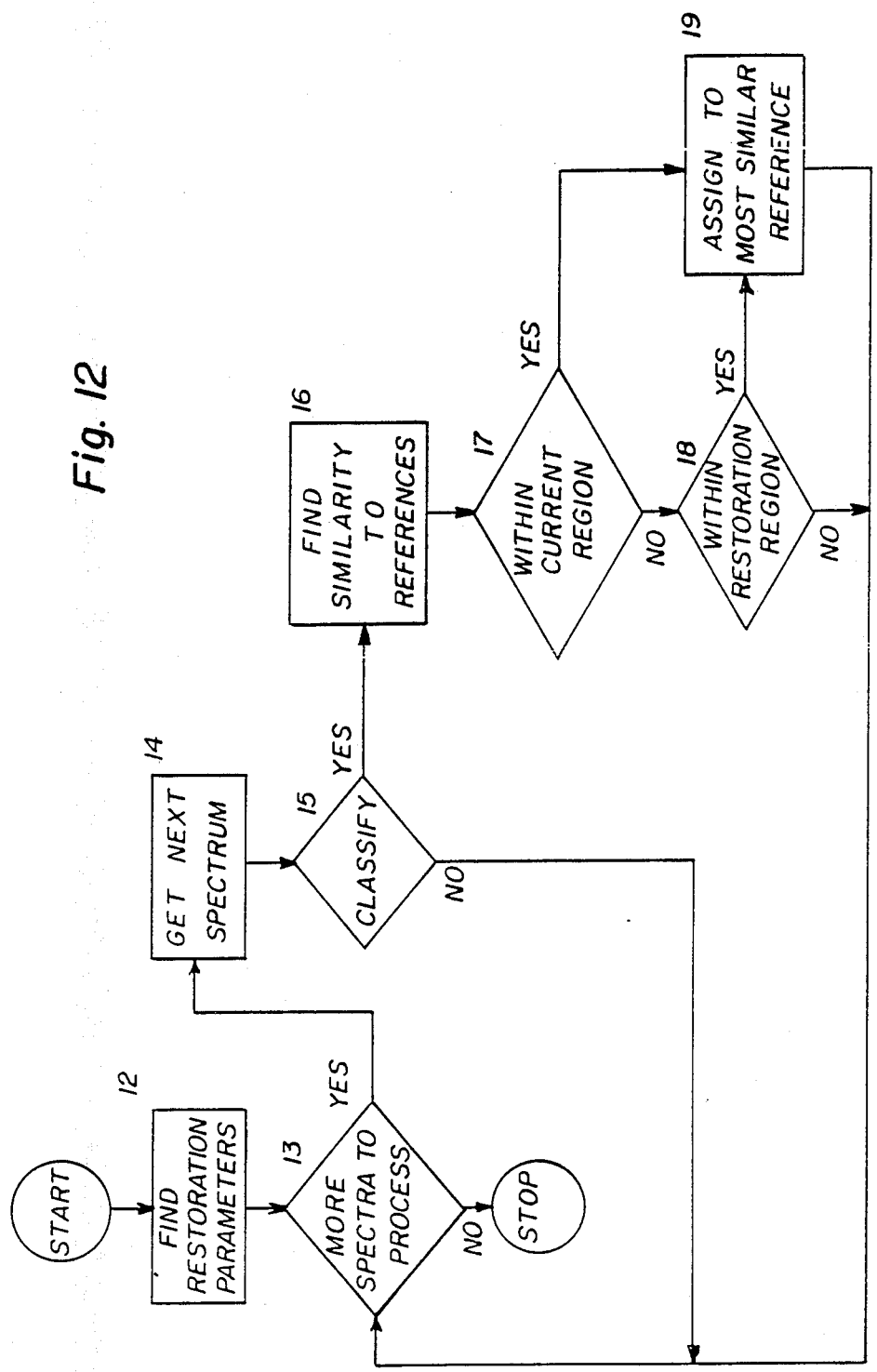
FIG. 12 is a flow chart of the restoration algorithm used in the method of this invention.
Figure 13:
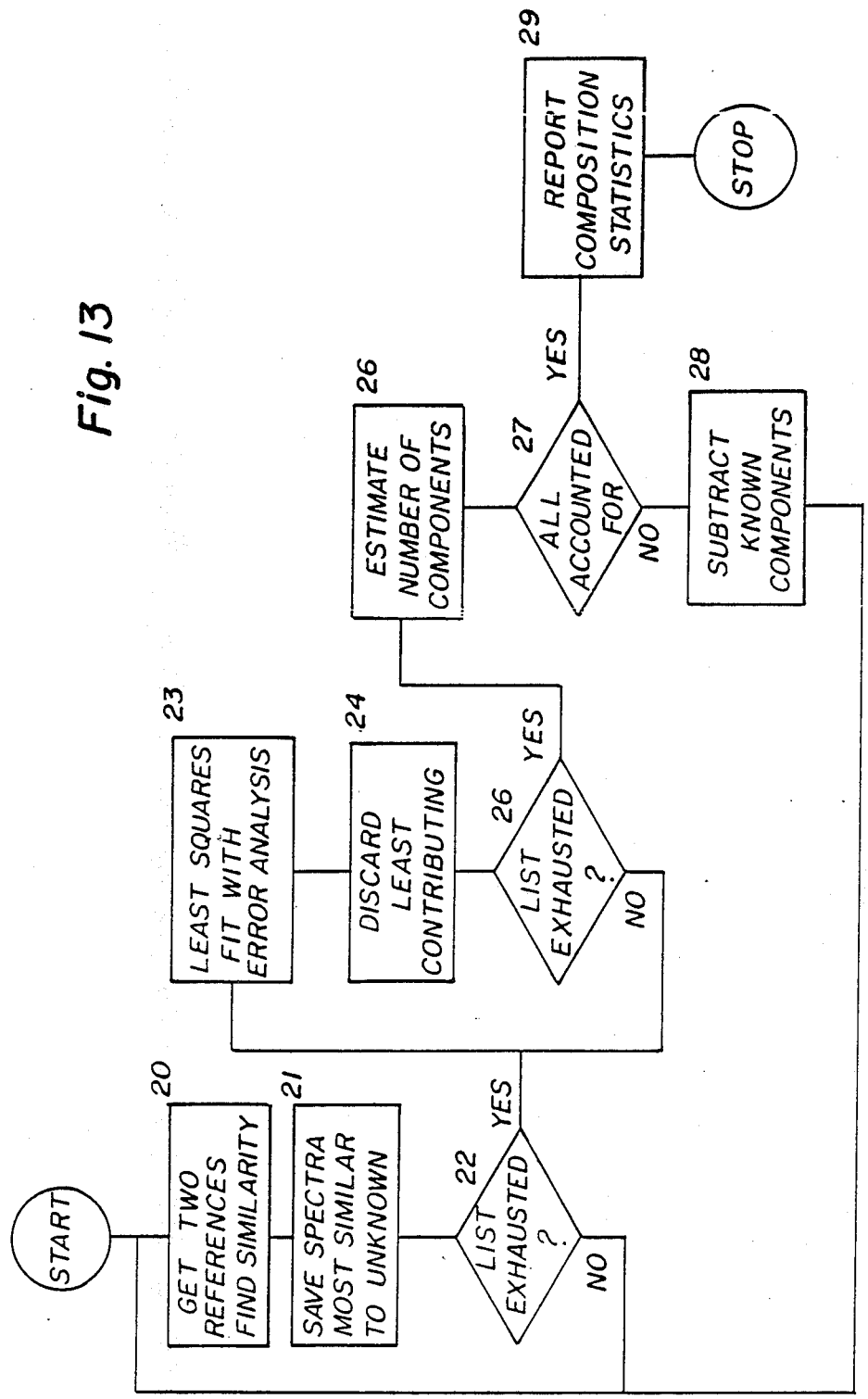
FIG. 13 is the search algorithm used in the method of this invention.

The implementation of these mathematical concepts perhaps will be more easily understood by considering the flow charts of FIGS. 11, 12 and 13. These flow charts describe the method used firstly to organize the hierarchial library, next to restore the data spectrum contained therein and finally to search the data base to identify an unknown spectra.

Data Base Organization

FIG. 11 shows the main steps of the data base organization procedure. It is assumed that a data base with some number of stored spectra is provided or known at the start. Each spectrum is viewed as a vector in an N (the number of data points per spectrum) dimensional space. The vectors are normalized to the unit vector before any operation is performed. Therefore, each spectrum represents a point on the surface of a hypersphere of unit radius in the N dimensional space.

In step 1 the vector sum of all spectra is calculated and normalized to the unit vector. This provides a starting spectrum for the procedure and counts the total number of spectra to be processed.

Steps 2 and 3 are computation routing tests. In step 5 a reference spectrum is selected. It is desirable that this reference be representative of a populated region in the vector space. Regional population density is assured by using a central vector, the mean unit vector, as the starting spectrum. That central vector is provided to step 5 by step 1 or a previous reference selection.

Two spectra are compared by measuring the angle between their vectors. This angle is always less than 90 degrees due to the imposed conditions of positive optical densities. The cosine of the angle becomes the similarity metric, with a value of 1.0 indicating identical spectra and a value of 0.0 indicating complete nonsimilarity or orthogonality.

Starting with the central vector, the similarity of all vectors to that given reference is calculated to find the vector closest to it, that is, the vector with the largest measure of similarity. The outcome is used as input, and the calculations are repeated, with the most similar subgroup of spectra, until the spectrum found is the nearest neighbor of its nearest neighbor.

Two spectra are named nearest neighbors if they are more similar, with larger similarity metric, to each other than to any other vector in the neighborhood (close vicinity on the hypersphere surface). The outcome of the algorithm is saved as a reference spectrum representing a populated region in hyperspace.

A second reference spectrum is found by applying the same selection procedure to a temporary subset of the original data base. This subset, composed of the spectra with low similarity metric values when compared to the first reference, is found in step 6. The operation in step 7 calculates the mean unit vector, repeating with the above subset of spectra, with the algorithm used in step 1. The second reference is found in step 8, which repeats the algorithm used in step 5, and completes the search for two nearly orthogonal vectors. These vectors, or spectra, share a low similarity metric value and are distant points in hyperspace.

Once two representative references have been found, the algorithm proceeds to reassign all spectra to one of two groups, in Step 9, according to their greatest similarity to either the first reference or the second reference spectrum. The starting data base is thus divided into two subgroups, each associated with a reference spectrum. These subgroups are provided as (sub)data bases for the next iteration, which will find an additional reference.

It is apparent that the number of fractions of the hyperspace will, eventually, induce possible erroneous or misassignments of spectra. A close neighborhood restoration algorithm is implemented along with the subdivision mechanism in step 9 to insure that all references do indeed represent their neighborhood.

The restored spectra will, thereafter, appear in more than one subdivision. Several iterations later, restored spectra will become references heading one or more subgroups of the original data base, which is tested for in step 10. In the event of the reference being assigned more than one subgroup, these subdivisions will represent different facets of the close neighborhood of the reference and are merged in step 1.

After steps 10 and 11, the process is repeated for each subgroup or (sub)data base of spectra. The number of subdivisions will grow exponentially (powers of 2) and so will the stored references. Since the references are excluded from the (sub)data bases they represent, the iterations will stop when all the spectra in the original data base have been stored as references. All subgroups reaching step 3 with less than 3 entries, fall out to step 4 where the existing entries are simply stored as references with no associated subsets.

Restoration Algorithm

FIG. 12 shows a flow chart of the restoration algorithm which is an expansion of step 9. In FIG. 12 the restoration parameters are calculated. For restoration purposes, the close neighborhood is defined as lying within a solid angle in the hyperspace of angular aperture equal to one half the angle formed by the reference patterns. The availability of more spectra is tested in step 13, and the next spectrum is read from memory in step 14. If this spectrum has already been stored as a reference, it is ignored in step 15, otherwise the similarity to the current reference is found in step 16. If the vector is within the current region (step 17) or within the restoration region (step 18), the spectrum is assigned to the most similar of the current references in step 19. At the end of this procedure, each entry or member of the data base will have been assigned or linked with a "predecessor" and two "successors". Of the later, the first is a near neighbor with high similarity to that entry, and the second successor will be a far neighbor with low similarity to the entry. This information constitutes the data base organization link structure and will be used, thereafter, in the unknown spectra identification procedure.

DATA BASE SEARCH

Given an unknown spectrum, a search for closely matching spectra is performed as shown in FIG. 13. The similarity of the unknown to the first two reference spectra is calculated in step 20. Since these references were selected from two distant and densely populated (sub) regions in the vector space, these comparisons statistically determine the path towards finding the region of hyperspace to which the unknown belongs. The references most similar to the unknown are saved for the final identification process. The next two references to be compared are taken from the (sub) section of the data base that is associated to the reference found to be most similar to the unknown, in step 21.

In each iteration, this process is repeated until reaching the last reference in this path, that is, the reference that has no spectra associated to it, as tested for in step 22.

Identification and Composition

In the final steps of the identification process, the accumulated most similar spectra are subjected to an iterative least square fit procedure (23). At the end of each iteration, the spectrum that least contributes to the unknown is discarded (24). The calculations are repeated until, as tested in step 25, all spectra (minus the number of search iterations) have been discarded.

The data base search and the identification process is repeated until a pre-established confidence level is reached in step 26. For each iteration, an additional component is found and in 28 subtracted from the unknown. The remainder is submitted to step 20 of the data base search, but the full unknown is resubmitted to the identification process.

Error analysis, in steps 23 and 26, provides the confidence information required in step 27 for the determination of the number of iterations needed and the number of components, if more than one, in the unknown spectrum.

All conditions satisfied, a report on the findings is generated in step 29 and together with statistical information provided to the user.

There has just been described a relatively simple method of establishing a hierarchial library of spectral data which can be used for identifying patterns based upon similarity criteria with an established library organized in accordance with the method of this invention, each vector representing a particular spectrum with a predecessor vector and two successor vectors which very quickly permit an unknown vector to track the hierarchy until its identity is established. The method permits the use of a microcomputer and also requires relatively little storage capacity.

What is claimed is:

1. A method of establishing a hierarchial library of spectra, each spectrum corresponding to point-by-point representations of characteristics of a known sample, each spectrum being different from all other spectra, comprising the steps of:

(a) converting each spectrum into a vector in n-dimensional hyperspace corresponding to the point-by-point representations of a different known sample;

(b) determining mathematical angles, as determinitive of similarity, between all of the vectors;

(c) selecting a first vector which is closest to a mean of the vectors and hence represents a center of population of the vectors;

(d) selecting a second vector which is most dissimilar to the first vector and represents a local center of population;

(e) separating the vectors into first and second groups of vectors that are most similar to the selected first and second vectors;

(f) for each group of vectors, excluding each previously selected vector representing a center of population and selecting one new vector that represents a local center of population and another vector that is most dissimilar to the one vector and which represents a local center of population of vectors;

(g) separating the vectors of each group into pairs of subgroups according to their similarity to the centers of population vectors of step (f);

(h) associating the center of population vector for each group of vectors for each subgroup of vectors; and (i) repeating steps (f), (g), and (h) for each successive subgroup until all vectors have been selected as centers of population.

2. The method of establishing a hierarchial library of spectra as set forth in claim 1 wherein in the separation of step (g) all vectors within a predetermined mathematical angle of each center of population vector of step (f) are included in each respective subgroup such that some vectors are involved in both subgroups.

3. The method of establishing a hierarchial library of spectra as set forth in claim 2 which includes the step of storing information in the library linking all associated vectors.

4. The method of establishing a hierarchial library of spectra as set forth in claim 3 which includes the steps of merging subgroups represented by a selected vector having a link to a common selected vector.

5. The method of establishing a hierarchial library of spectra as set forth in claim 4 wherein similarity of vectors is determined by an inner product between the vectors.

6. The method of identifying the spectrum of a unknown sample using the hierarchial library of spectra established by the method of claim 5 comprising the steps of:

(j) converting the spectrum of the unknown sample into an unknown vector corresponding to a point-by-point representation of the unknown sample;

(k) determining the similarity between the unknown vector and the first and second vectors;

(l) determining the similarity between the unknown vector and the center of population vectors for the subgroups associated with the more similar one of the first and second vectors; and (m) determining the similarity between the unknown vector and each successive pairs of vectors for the subgroups associated with the more similar higher order subgroup until there are no further associated subgroups, the unknown spectrum being determined by the most similar vector compared.

7. The method of establishing a hierarchial library of spectra, each point representation having a coordinate value according to the sample characteristic, each vector having an amplitude which is equal to the square root of the sum of the squares of the coordinate values p, as set forth in claim 2 wherein the mean of the vectors (C) of step (c) is determined by $$C = (c_1, c_2, c_3, \ldots c_N) \text{ where}$$

$$c_i = \text{SUM} (p_{ij}/|V_j|)$$

where $i = 1, 2, 3, \ldots N$ and
$j = 1, 2, 3, \ldots M$, where N is the points in each spectrum and p is the value of the sample spectrum at each point, M is the number of vectors in the library, and $|V_j|$ is the vector amplitude.

8. The method of identifying the spectrum of an unknown sample using the heirarchial library of spectra as set forth in claim 3 comprising the steps of:

(j) converting the spectrum of the unknown sample into an unknown vector corresponding to a point-bypoint representation of the unknown sample;

(k) determining the similarity between the unknown vector and the first and second vectors;

(l) determining the similarity between the unknown vector and the center of population vectors for the subgroups associated with the more similar one of the first and second vectors; and (m) determining the similarity between the unknown vector and each successive pairs of vectors for the subgroups associated with the more similar higher order subgroup until there are no further associated subgroups, the unknown spectrum being determined by the most similar vector compared.

9. The method of establishing a hierarchial library of spectra as set forth in claim 1 which includes the step of storing information in the library linking all associated vectors.

10. The method of establishing a hierarchial library of spectra as set forth in claim 9 which includes the steps of merging subgroups represented by a selected vector having a link to a common selected vector.

11. The method of establishing a hierarchial library of spectra as set forth in claim 10 wherein similarity of vectors is determined by an inner product between the vectors.

12. The method of identifying the spectrum of an unknown sample using the hierarchial library of spectra established by the method of claim 11 comprising the steps of:

(j) converting the spectrum of the unknown sample into an unknown vector corresponding to a point-bypoint representation of the unknown sample;

(k) determining the similarity between the unknown vector and the first and second vectors;

(l) determining the similarity between the unknown vector and the center of population vectors for the subgroups associated with the more similar one of the first and second vectors; and (m) determining the similarity between the unknown vector and each successive pairs of vectors for the subgroups associated with the more similar higher order subgroup until there are no further associated subgroups, the unknown spectrum being determined by the most similar vector compared.

13. The method of establishing a hierarchial library of spectra as set forth in claim 1 wherein similarity of vectors is determined by an inner product between the vectors.

14. The method of establishing a hierarchial library of spectra as set forth in claim 13, each point representation having a coordinate value according to the sample characteristic, each vector having an amplitude which is equal to the square root of the sum of the squares of coordinate values p, wherein the mean of the vectors (C) of step (c) is determined by $$C = (c_1, c_2, c_3, \ldots c_N) \text{ where}$$

$$c_i = \text{SUM} (p_{ij}/|V_j|)$$

where $i = 1, 2, 3, \ldots N$ and
$j = 1, 2, 3, \ldots M$, where N is the number of sampling points in each spectrum, p is the value of the sample spectrum at each point, M is the number of vectors in the library, and $|V_j|$ is the vector amplitude.

15. The method of identifying the spectrum of an unknown sample using the hierarchial library of spectra as set forth in claim 14 comprising the steps of:
   (j) converting the spectrum of the unknown sample into an unknown vector corresponding to a point-by-point representation of the unknown sample;
   (k) determining the similarity between the unknown vector and the first and second vectors;
   (l) determining the similarity between the unknown vector and the center of population vectors for the subgroups associated with the more similar one of the first and second vectors; and
   (m) determining the similarity between the unknown vector and each successive pairs of vectors for the subgroups associated with the more similar higher order subgroup until there are no further associated subgroups, the unknown spectrum being determined by the most similar vector compared.

16. The method of establishing a hierarchical library of spectra, each point representation having a coordinate value according to the sample characteristic, each vector having an amplitude which is equal to the square root of the sum of the squares of the coordinate values p, as set forth in claim 1 wherein the mean of the vectors (C) of step (c) is determined by $$C = (c_1, c_2, c_3, \ldots c_N) \text{ where}$$

$$c_i = \text{SUM} (p_{ij}/|V_j|)$$

where $i = 1, 2, 3, \ldots N$ and
$j = 1, 2, 3, \ldots M$, where N is the points in each spectrum and p is the value of the sample spectrum at each point, M is the number of vectors in the library, and $|V_j|$ is the vector amplitude.

17. The method of identifying the spectrum of an unknown sample using the hierarchial library of spectra established by the method of claim 1 comprising the steps of:
   (j) converting the spectrum of the unknown sample into an unknown vector corresponding to a point-by-point representation of the unknown sample;
   (k) determining the similarity between the unknown vector and the first and second vectors;
   (l) determining the similarity between the unknown vector and the center of population vectors for the subgroups associated with the more similar one of the first and second vectors; and
   (m) determining the similarity between the unknown vector and each successive pairs of vectors for the subgroups associated with the more similar higher order subgroup until there are no further associated subgroups, the unknown spectrum being determined by the most similar vector compared.

18. A method of establishing a hierarchial library of spectra, each spectrum corresponding to point-by-point representations of characteristics of a known sample, each spectra being different from all other spectra, comprising the steps of:
   (a) converting each spectrum into a vector in n-dimensional hyperspace corresponding to the point-by-point representations of a different known sample;
   (b) determining mathematical angles, as determinitive of similarity between all of the vectors;
   (c) selecting a first vector which is closest to a mean of the vectors and hence represents a center of population of the vectors;
   (d) selecting a second vector which is most dissimilar to the first vector and represents a local center of population;
   (e) with the selected vectors excluded, selecting a pair of vectors which are representative, respectively (1) of a center of population closest to a mean of the remaining vectors, and (2) of a local center of population most dissimilar to the center of population of (1);
   (f) separating the vectors of each group into pairs of subgroups according to their similarity and dissimilarity to the center of population vectors of step (e);
   (g) associating a center of population vector for each subgroup of vectors with the center of population vector of its ancestor group; and
   (h) repeating steps (e), (f), and (g), for each successive subgroup until all vectors have been selected as centers of populations.

19. The method of establishing a hierarchial library of spectra as set forth in claim 18 which includes the step of storing information in the library linking all associated vectors.

20. The method of identifying the spectrum of an unknown sample using a hierarchial library of spectra as set forth in claim 18 comprising the steps of:
   (j) converting the spectrum of the unknown sample into an unknown vector corresponding to a point-by-point representation of the unknown sample;
   (k) determining the similarity between the unknown vector and the first and second vectors;
   (l) determining the similarity between the unknown vector and the center of population vectors for the subgroups associated with the more similar one of the first and second vectors; and
   (m) determining the similarity between the unknown vector and each successive pairs of vectors for the subgroups associated with the more similar higher order subgroup until there are no further associated subgroups, the unknown spectrum being determined by the most similar vector compared.

* * * * *